(12) United States Patent
Galehr

(10) Patent No.: US 8,443,502 B2
(45) Date of Patent: *May 21, 2013

(54) BLANK ARRANGEMENT

(75) Inventor: Klaus Galehr, Schlins (AT)

(73) Assignee: Ivoclar Vivadent AG, Schaan (LI)

( * ) Notice: Subject to any disclaimer, the term of this patent is extended or adjusted under 35 U.S.C. 154(b) by 212 days.

This patent is subject to a terminal disclaimer.

(21) Appl. No.: 12/587,397

(22) Filed: Oct. 6, 2009

(65) Prior Publication Data

US 2010/0028834 A1  Feb. 4, 2010

Related U.S. Application Data

(63) Continuation-in-part of application No. 12/231,121, filed on Aug. 29, 2008.

(30) Foreign Application Priority Data

Sep. 14, 2007 (DE) .......................... 10 2007 043 837

(51) Int. Cl.
*B25B 27/41* (2006.01)
*A61C 11/00* (2006.01)

(52) U.S. Cl.
USPC .......................................... 29/281.1; 433/49

(58) Field of Classification Search ................ 29/281.1, 29/557, 896.1; 433/49, 213, 201.1; 409/219, 409/234; 269/287; 426/542.8; 428/542.8

See application file for complete search history.

(56) References Cited

U.S. PATENT DOCUMENTS

| 4,615,678 | A | 10/1986 | Moermann et al. |
|---|---|---|---|
| 5,342,696 | A | 8/1994 | Eidenbenz et al. |
| 6,224,371 | B1 | 5/2001 | de Luca |
| 6,485,305 | B1 | 11/2002 | Pfeiffer |
| 6,627,327 | B2 | 9/2003 | Reidt et al. |
| 6,640,150 | B1 * | 10/2003 | Persson et al. ................ 433/213 |
| 6,660,400 | B1 * | 12/2003 | Hintersehr ................ 428/542.8 |
| 6,905,293 | B1 | 6/2005 | Filser et al. |
| 6,991,853 | B2 | 1/2006 | de Luca et al. |
| 7,077,391 | B2 | 7/2006 | Filser et al. |
| 7,214,435 | B2 | 5/2007 | Meyertholen et al. |
| 7,255,562 | B2 | 8/2007 | Rusin et al. |
| 2004/0120781 | A1 * | 6/2004 | Luca et al. ...................... 29/557 |
| 2005/0008989 | A1 | 1/2005 | Rothenberger et al. |
| 2005/0276672 | A1 * | 12/2005 | Prince et al. .................. 409/234 |
| 2007/0172787 | A1 | 7/2007 | Fornoff |

FOREIGN PATENT DOCUMENTS

| DE | 197 33 161 A1 | 2/1999 |
|---|---|---|
| DE | 102004020192 | 10/2005 |
| DE | 19714223 | 12/2005 |
| EP | 0 160 797 A1 | 11/1985 |
| WO | 02/09612 A1 | 2/2002 |

* cited by examiner

*Primary Examiner* — Hadi Shakeri

(74) *Attorney, Agent, or Firm* — Ann M. Knab; Thad McMurray

(57) ABSTRACT

This invention relates to a blank arrangement, with a blank (22) that is to be machined, in particular for the production of dental restoration parts. The blank is connected to a holder (16), which is fixedly connected to the blank (12), and to an adapter (22), which releasably bears the holder (16) and the blank (12), the adapter (22) having an effective surface by means of which the blank unit can be mounted in or on the work holding fixture of a machining device.

23 Claims, 6 Drawing Sheets

BLANK ARRANGEMENT

CROSS-REFERENCE TO RELATED APPLICATIONS

This application is a continuation-in-part of U.S. application Ser. No. 12/231,121 filed Aug. 29, 2008, which in turn claims foreign priority benefits under 35 U.S.C. §119 from German patent application Ser. No. 10 2007 043 837.2 filed Sep. 14, 2007.

TECHNICAL FIELD

The invention relates to a blank arrangement, in particular for the production of dental restoration parts, with a blank that is to be machined, in particular made of dental material and suitable for the production of dental restoration parts, the blank being adhesively secured to a holder which has a portion received within an adapter.

BACKGROUND OF THE INVENTION

Blanks for dental restoration parts are typically machined, in order to achieve an adaptation to the desired shaping. While precision work and adjustments have to be performed in the adaptation of the dental restoration part by the dentist, or generally by the dental technician, typically blanks produced in block form are brought into shape in advance, in order to restrict the adaptation work to a reasonable amount.

This applies to a particular extent to dental restoration parts and corresponding blanks made of ceramic. Ceramic materials—especially zirconium dioxide—are particularly hard, so that it is desirable to reduce the machining that has to be performed in the dental laboratory to a minimum.

On the other hand, ceramic blanks can be produced exceedingly well in block form. Therefore, based on the suitably selected raw material, a blank is pressed in block form and sintered in a sintering furnace.

With regard to the particular hardness of ceramics, such as for example zirconium-based ceramics, it has also already become known not to machine the fully sintered product, which is very hard, but a pre-sintered product, which already has sufficient stability for machining. As a result, the wear of the tools that are used for the machining, that is to say for example milling cutters or turning tools, can also be distinctly reduced.

For the machining, the blank must be received in a suitable way in the work holding fixture of the machining device. Often used for this purpose is a holding pin, the outer shape of which is formed suitably for the work holding fixture and is cemented in a bore in the blank. See for example U.S. Pat. Nos. 6,224,371 and 6,627,327. However, to this extent the anchoring of the blanks for the machining is extremely complicated and also susceptible to errors. In particular, it must be ensured that a predetermined position is ensured for the fixing between the pin, which is held in the work holding fixture, and the blank.

Furthermore, it has also already been proposed to configure a support with an adhesive area, on which the blank is adhesively attached. See for example U.S. Pat. Nos. 4,615,678, 7,214,435, and 7,255,562. This also allows in particular blanks of different sizes to be used with the same work holding fixture fixing pin. Typically, such an adhesive area is planar, in order to ensure a particularly good contact with a surface of the blank, which is initially in block form. As a result of this, the spatially fixed fixing of the blank is difficult, and it is typical in the case of such a configuration to resort to forming a differential dimension, which relates a side face of the blank to a side face of the insert pin, and using this as a basis for fixing the connection between the insert pin and the blank. This is indeed possible in principle and can also be automated by machine, which is necessary with regard to the numbers of items to be produced.

However, precisely in the case of different work holding fixtures, it is necessary to use different insert pins, which accordingly have different dimensions. However, the combination of such different insert pins, in a number corresponding to the work holding fixtures used, with different blanks leads to a multiplication of the possible combinations, so that fixing such a differential value would be significantly too complicated in practice and therefore this has not been widely adopted for understandable reasons.

It has also been proposed to provide a blank which is attached to a support plate mounted on a holder section that is received by a boring inside a shaft part of a holding device. See German Patent 197 33 161. In this design a clamping screw is used to fix the holder section into position. A groove extending around the outside of the holder section mantle receives at least part of the screw, which is smaller than or equal in size to the groove.

OBJECTS AND SUMMARY OF THE INVENTION

Therefore, the invention is based on the object of providing a blank arrangement with a blank that is to be machined, in particular made of dental material and suitable for the production of dental restoration parts, that is also reliably suitable for the industrial-scale production of adapted, that is to say machined, blanks.

According to the invention, it is particularly favorable that, by providing a separate holder, a unique assignment between the relative position of the blank and a reference point of the holder that is to be arbitrarily chosen is possible. This is in principle independent of a configuration of an effective surface of the adapter provided according to the invention, which ensures engagement with respect to the work holding fixture. The effective surface can consequently be kept in any desired suitable form, and even be complicated, so that it is possible to make it compact, without having to pay any regard to the dimensioning and relative arrangement of the blank.

Blanks of various sizes can accordingly be readily attached centrally on an end face of the holder and adjusted with respect to the shank of the latter. Once the relative position of the shank, which is guided in a corresponding recess in the adapter, is known for each configuration of the adapter, and consequently the corresponding work holding fixture, the number of dimensionings required according to the invention is still practicable. If, for example, 20 different work holding fixtures are to be combined with 30 different blanks, the provision of the sum of the corresponding dimensions, that is to say 50 dimensions, is required according to the invention, while theoretically, in the case of solutions without the invention that have a corresponding number of work holding fixtures and blanks, 20×30, that is to say 600, sizes would have to be kept in stock, which is out of the question in practice. It is surprisingly found according to the invention that the division into a holder and an adapter reduces the organizational effort involved.

According to the invention, the holder may be fastened to the blank in any desired suitable way. For example, the blank may laterally protrude distinctly beyond the holder and be placed on an end face of a plate which closes off the holder at the top.

It is particularly favorable according to the invention that the holder, which carries the blank, and can be handled separately from the adapter, allows a connection that can always be established with the same automatic adhesive dispenser to be established between the holder and the blank. To this extent, the automatic adhesive dispenser therefore does not have to be converted, or a new dispenser obtained, when blanks for other work holding fixtures are to be handled. This represents a considerable advantage specifically in the case of the industrial production of dental restoration parts in large numbers, specifically also in the case of the use of ceramic blocks as blanks.

The blank arrangement according to the invention has with preference an adapter which is provided with always the same receptacle for the holder. This ensures that blanks can be securely held in the work holding fixture independently of the shaping of the work holding fixture. Surprisingly, the security is not impaired by the additional connection having to be established between the holder and the adapter. The accuracy of the fit with which the adapter receives the holder is chosen with preference such that, when the connection is established, the holder and the adapter act virtually as one piece, even if a separation is in fact possible. If need be, the securement can be further improved by a partially resilient configuration of the transition between the holder and the adapter, it being self-evident that a comparatively hard spring is used with preference, one which can withstand the machining forces of the tool of the machining device.

It is particularly favorable according to the invention whenever the holder is designed such that it can transfer shearing forces particularly well, both with respect to the adapter and with respect to the blank. For this purpose, it is possible for example to allow a short and comparatively sturdy connector to enter a blind-hole bore of the adapter, to be precise with exact-fitting guidance. The force transfer with respect to the blank can be further assisted by the adapter having lateral supporting flanges in the form of a collar, which provides solid support for a plate or a corresponding flange of the holder there. Compressive forces, that is to say forces in the axial direction, can also be absorbed well in this way.

In the case of this embodiment, the receptacles between the holder and the adapter have virtually the form of 'T"s, which are inserted one in the other.

It is self-evident that any other desired configuration of the holder and the adapter and their transition is possible. By providing a comparatively thin supporting surface of the holder, which is supported by a corresponding supporting collar or an end face of the adapter, a wide end face of the holder can also be provided as an adhesive area with comparatively little expenditure in terms of material.

The blank, the holder and the adapter may be shaped here in any suitable way desired. Both round configurations and configurations deviating from a circular shape are possible in each case, but it is in any event preferred that the connection between the adapter and the holder is fixed in terms of rotation and secure in terms of moments, that is to say withstands both shearing forces and rotational forces that may be introduced into the blanks by the machining device during the machining.

It is particularly favorable according to the invention if an end face of the holder provides an area that is flat and to which adhesive adheres well, the extent of which corresponds at least to the extent of the ceramic block (considered in the respective direction). This ensures that a supporting surface that is as large as possible is available for the adhesive connection, since lateral machining forces on the blank must be absorbed by the adhesive connection, so that a wide contact area between the holder and the blank reduces the forces of detachment.

It is particularly favorable according to the invention if the pluggability of the holder into or onto the adapter is provided by simple means and the release of the connection is also quickly possible as and when required. Any desired suitable connecting techniques are suitable for this purpose, it being self-evident that it is particularly favorable if rotational forces can also be transferred in a way that is secure in terms of moments.

It is particularly favorable according to the invention that the holder for the blank has an end face that faces away from the adapter and on which the blank can be received.

It is particularly favorable according to the invention that the holder has a round or angular plate, the face of which that faces away from the adapter carries the blank.

It is particularly favorable according to the invention that the blank is fastened to the holder with surface area contact and protrudes beyond the holder at least one point.

It is particularly favorable according to the invention that the blank is fastened to the holder with an interference fit.

It is particularly favorable according to the invention that the blank is adhesively attached, welded and/or bonded on the holder.

It is particularly favorable according to the invention that the blank and the holder are at least partially pressed one into the other or screwed one onto the other or in some other way connected to each other with a form fit.

It is particularly favorable according to the invention that the holder and the blank are braced against each other and that the pre-stressing of the bracing is in particular greater than the machining force produced by the machining device.

It is particularly favorable according to the invention that the holder has a connecting region for the blank, which in particular offers flange-like projections and is formed with particular preference in the form of a plate and from which there extends a shank, which interacts with the adapter.

It is particularly favorable according to the invention that the holder has a shank which is formed for being received in the adapter, in particular for being received in the adapter with a form fit. It is particularly favorable according to the invention are the holder is fixed with respect to the adapter in a rotationally locked manner and in particular has a stop facing in the axial direction.

It is particularly favorable according to the invention that the shank is received in a blind hole of the adapter, in particular in the upper region thereof.

It is particularly favorable according to the invention that the shank of the holder ends above an undercut, which forms an effective surface with respect to the work holding fixture of the machining device and, in particular, offers a form fit there.

It is particularly favorable according to the invention that the shank of the holder has at least one undercut, which in particular runs at least partially around it.

It is particularly favorable according to the invention that the holder, in particular its shank, has a bore or an internal thread for the fixing in the adapter, which in particular matches a through-bore in the adapter.

It is particularly favorable according to the invention that the holder, in particular its shank, the adapter and/or the blank have a marking, in particular a mechanical or colored marking, which symbolizes the fitting together of corresponding parts of the blank arrangement.

It is particularly favorable according to the invention that the holder, in particular it shank, the adapter and/or the blank have a barcode, in particular a mechanical or colored barcode, which symbolizes the fitting together of corresponding parts of the blank arrangement.

It is particularly favorable according to the invention that the holder, in particular its shank, the adapter and/or the blank have a sensor, a transmitter and/or a chip, by means of which the use of the respectively relevant type of blank, holder and/or adapter can be signaled.

It is particularly favorable according to the invention that the holder and/or the adapter have a predetermined breaking point, which yields under loading in the machining device.

It is particularly favorable according to the invention that at least two adapters are provided and have different effective surfaces that can be inserted into the work holding fixtures of different machining devices, and wherein the at least two adapters have receptacles that are the same as each other for the holder.

It is particularly favorable according to the invention that the connection between the holder and the adapter is secured such that it is free from vibrations.

According to a further advantageous configuration, it is provided that the blank is fastened to the holder with surface area contact and that the holder protrudes beyond the blank at least one point.

According to a further advantageous configuration, it is provided that the blank and the holder are at least partially pressed one into the other or screwed one against the other, or in some other way connected to each other.

According to a further preferred configuration, it is provided that the blank and the holder are fixedly connected to each other or fixedly braced one against the other such that the pre-stressing of the bracing or the holding force of the connection is greater than the machining force produced by the machining device.

According to a further advantageous configuration, it is provided that the blank arrangement according to the invention forms on the holder a flange, which is formed in particular in the form of a plate and from which there extends a shank or an insert stub, which interacts with the adapter.

According to a further advantageous configuration, it is provided that a shank of the holder is suitably formed for being received in the adapter, in particular for being received in the adapter with a form fit.

According to a farther advantageous configuration, it is provided that the shank is formed as an insert stub and is received in a receptacle or a blind hole of the adapter, in particular in the upper region thereof.

According to a further advantageous configuration, it is provided that the shank of the holder ends above an undercut, which forms the effective surface with respect to the work holding fixture of the machining device and, in particular, offers a form fit there.

According to a further advantageous configuration, it is provided that the holder and/or the blank and/or the adapter have a marking or a coding, which symbolizes the fitting together of corresponding parts of the blank arrangement. The marking may also be formed as a mechanical or colored barcode.

BRIEF DESCRIPTION OF THE FIGURES

Further advantages, details and features emerge from the following description of two exemplary embodiments of the invention on the basis of the drawing, in which.

DETAILED DESCRIPTION

Figure 1:
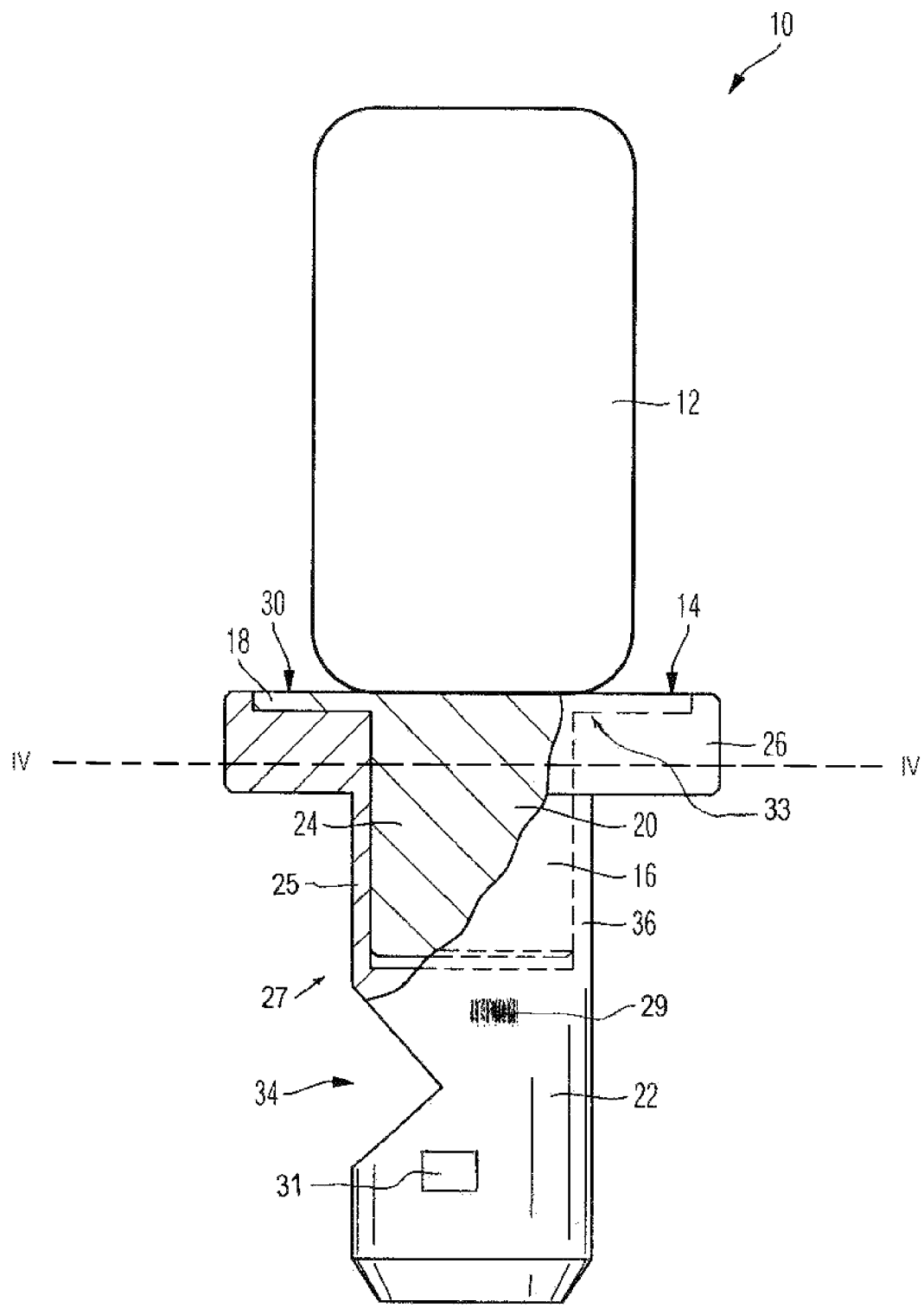
FIG. 1 shows a schematic side view of an embodiment of a blank arrangement according to the invention.
Figure 3:
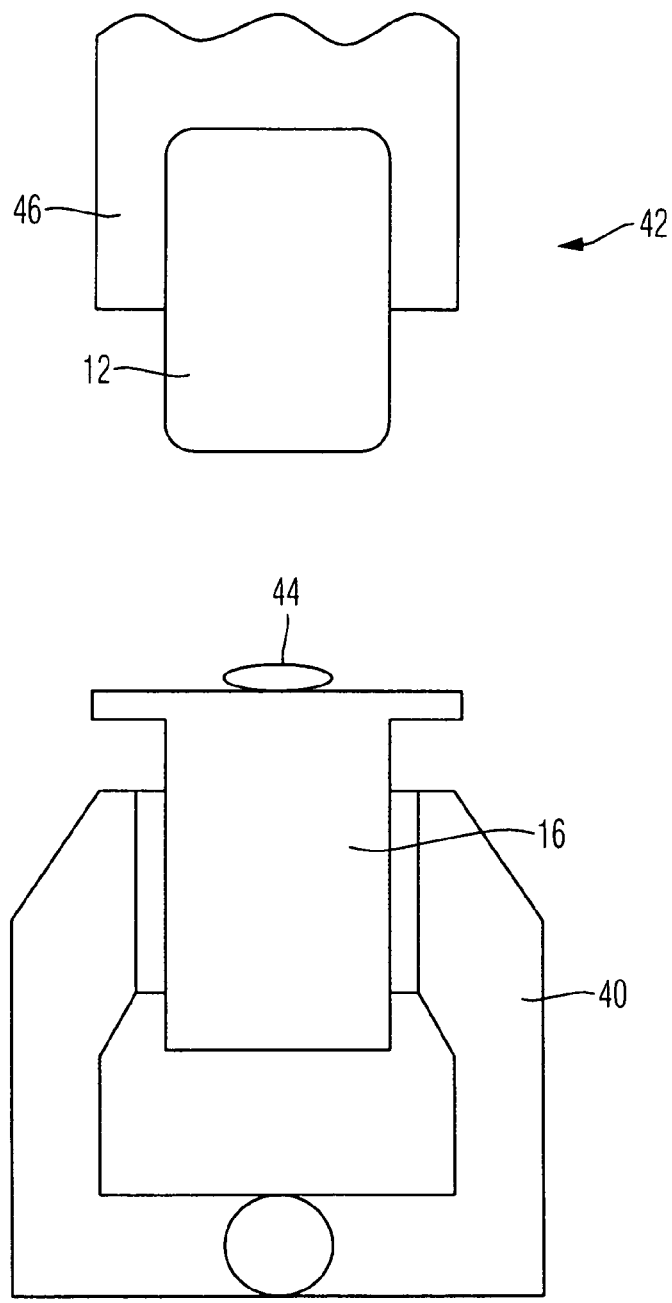
FIG. 3 shows a schematic view of an automatic adhesive dispenser for establishing a connection between the holder and the blank.

The blank arrangement 10 represented in FIG. 1 has a blank 12, which is adhesively attached on an end face 14 of a holder 16. The attachment is achieved by an automatic adhesive dispenser as it is shown in FIG. 3. With preference, the blank 12 is a cuboidal ceramic element with rounded corners. It is intended for being machined, in order to produce a dental restoration part. For this purpose, it lies with one of its side faces flush against the end face 14. The type of adhesive bonding that is used according to the invention is known in the prior art, it being self-evident that the holding forces of the adhesive connection distinctly exceed the forces that are introduced onto the blank during the machining.

The holder 16 is formed in a substantially T-shaped manner. It has a peripheral flange 18, the extent of which distinctly exceeds the width of the blank 12, so that blanks of distinctly greater dimensions can also be received there.

Furthermore, the holder 16 has an insert stub 20, which is substantially of the same height and width, or else—as in the exemplary embodiment represented—a length or height that exceeds the width by no more than 50%. In the exemplary embodiment represented, the height/width ratio is 1.4:1.

In the exemplary embodiment represented, the holder 16 is received in a completely recessed manner in the adapter 22. For this purpose, the adapter 22 has a receptacle 24, which is formed in the manner of a blind-hole bore and in its dimensions matches the insert stub 20. Accordingly, in the exemplary embodiment represented the receptacle 24 is formed as a blind hole.

As may be taken from FIG. 1, the blind hole 24 is formed in the upper portion of the adapter 22. The adapter 22, in this upper portion has side walls 25 which e.g. have a thickness of a tenth of the diameter of the stub 20. By this dimensioning, the upper portion 27 of the adapter 22 is structurally elastic and is intended to clamp and firmly hold the stub 20 of holder 16 in a press-fit arrangement. By this arrangement, the holder 16 may be removed from the adapter 22 but yet is firmly attached such that even miffing or other workloads on the blank 12 may be supported via the holder/adapter arrangement.

On the other hand, the stub 20 completely fills out the receptacle 24 which thus is stabilized such that the overall arrangement of the adapter 22 is stabilized when the holder 16 is received within the receptacle 24.

In this way, both mentioned parts interact with each other, and the holder 16 and the adapter 22 are fixedly connected to each other.

Figure 4:
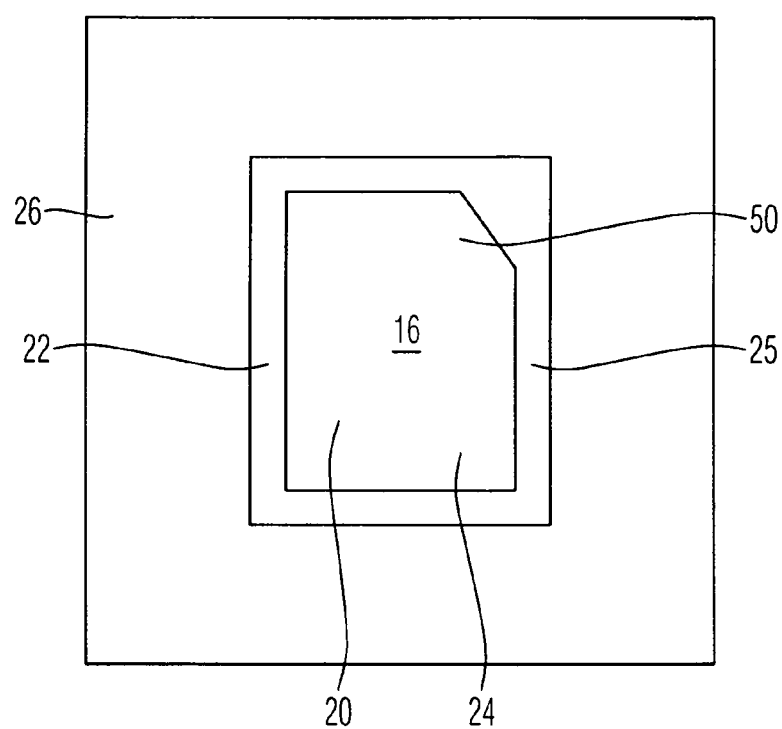
FIG. 4 shows a cross-sectional view through the holder and the adapter in a particular embodiment of the invention, this view being taken generally along the line IV-IV in FIG. 1.

As may be taken from FIG. 4, these parts are also rotationally locked by a arrangement which prevents them from being rotated against each other. This will be described in further detail with respect to FIG. 4.

Any suitable other connection between the holder and the adapter may be used. As an example, there may be only a part of the holder 16 under pressure by the adapter 22. Instead of the pressure connection, there may be screw connection or a releasable bonding connection between the mentioned parts.

Also, it is possible to arrange an undercut for a snap in connection between the holder 16 and the adapter 22. To facilitate the assignment of different adapters, it is possible to use a suitable coding or marking, in order to facilitate the handling of different adapters.

An important aspect of the invention is the possibility to pre-arrange a blank fixedly connected to the holder 16. According to the invention, the holder has a unique unified stub which may be combined with any possible adapters. Thus, there is no need to buy and arrange an automatic adhesive dispenser before milling the blank. Thus, it is no longer required that every dental laboratory has such an automatic adhesive dispenser; a milling machine is sufficient.

As may be taken from FIG. 1, a bar code 29 or any other marking may be use to identify the adapter. Additionally or alternatively, a sensor, a transmitter and/or a chip 31 may be build in the blank 12, the holder 16 or the adapter 22, in order to identify the adapter.

The holder 16—or alternatively the adapter 22—may have a predetermined breaking point 33 which uses the stress concentration or the notch effect in the transition between flange 18 and the stub 20.

Supporting the flange 18 of the holder 16, the adapter 22 also has a lateral supporting flange 26, which is formed in the manner of a collar and likewise give the adapter 22, when viewed in cross section, substantially the shape of a T. The supporting flange 26 of the adapter have a distinctly greater material thickness than the flange 18 of the holder, a ratio of 4:1 being provided for example, but a ratio between 2:1 and 10:1 also being possible.

In the exemplary embodiment represented, the flange 18 is also received in a recessed manner in a depression 30 of the supporting flange 26. Thus, the flange 18 is supported by the supporting flange 26. It is self-evident that this measure is optional. If such an arrangement is provided, it is also possible to form a means for preventing twisting between the holder 16 and the adapter 22 on the outer circumference of the flange 18 or on the outer circumference of the depression 30.

Alternatively, a means for preventing twisting may also be provided by corresponding shaping of the insert stub 20 and the receptacle 24, which is formed as a blind hole, in that these two parts are given a shape deviating from the shape of a circle, at least at one point.

In the exemplary embodiment represented, the adapter 22 is shaped in a particular way, in order to allow it to be received in a special work holding fixture of a machining device, which is not represented here. For this purpose, in the case of the example a right-angled notch 34 is formed as an undercut. The notch 34 extends under the blind hole 24, so that it does not impair the reception of the holder 16 there. Corresponding work holding fixtures are known and may be designed in any desired suitable way, with numerous different work holding fixtures being in existence, specifically dependent on the milling machine manufacturer.

If the blank 12 is to be machined in a machining device other than the one represented here, the adapter 22 can be readily exchanged, and replaced by another adapter 22, which however has exactly the same receptacle 24, so that the same holder 16 can be inserted.

The connection between the adapter 22 and the holder 16 is free from play, so that the removal of the holder 16 from the adapter 22 is possible merely with a certain force. In the exemplary embodiment represented, the lateral material thickness, of the adapter 22 around the insert stub 20 is quite small. The side wall 36 provided there may, if need be, also be prestressed inward, so that it curves inwardly somewhat when the holder 16 is not inserted. Receiving the holder 16 then has the effect that the side wall 36 lies under prestress against the side faces of the insert stub 20.

Since the same holder can always be used, the adapter can be adhesively attached extremely easily in an exact position on the holder. This can take place for example by the same degree of prestress of the flange 18 with respect to the insert stub 20 always being used, and the blank 12, the width of which is fixed and varies from blank to blank, being adhesively attached at a predetermined distance from the edge of the flange 18. It is also possible for such an adhesive connection to be provided by means of an automatic adhesive dispenser.

Figure 2:
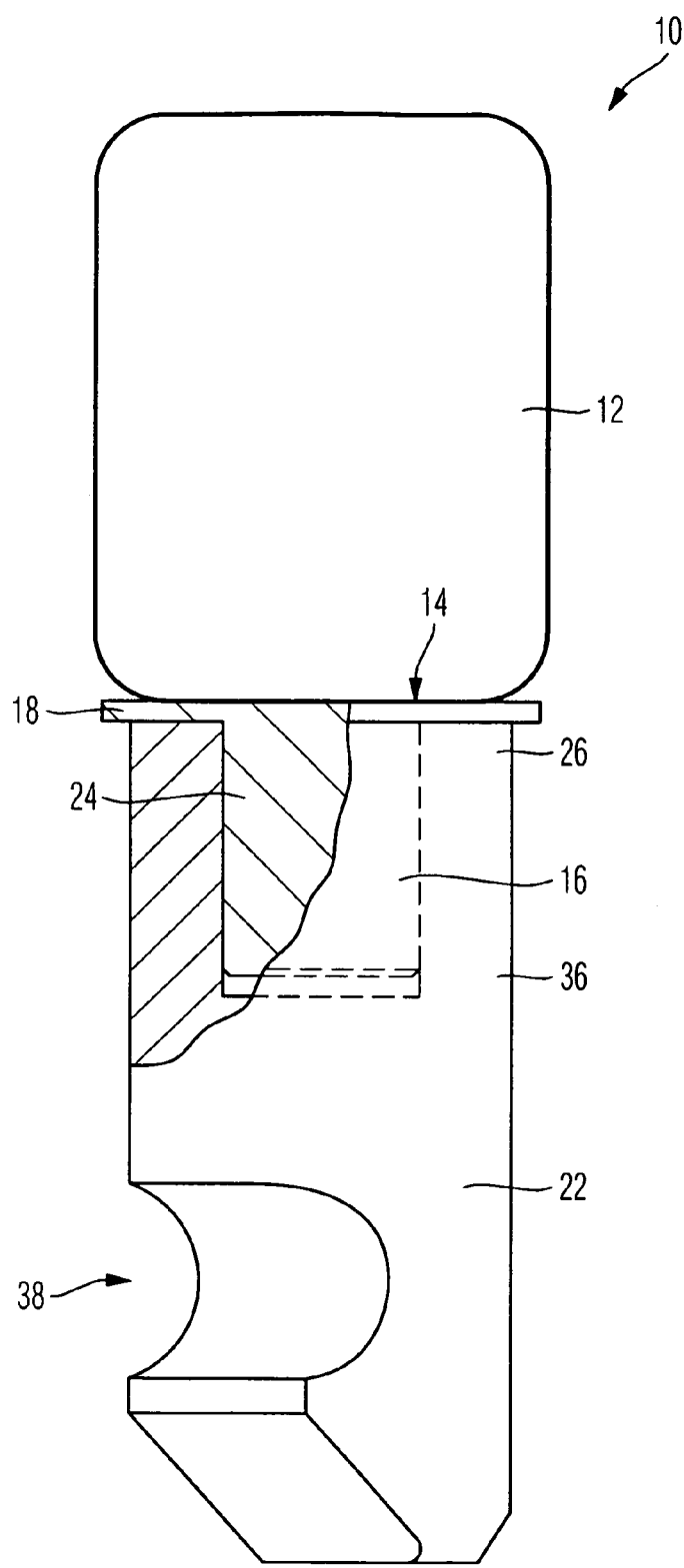
FIG. 2 shows a view of a further embodiment of a blank arrangement according to the invention.

A modified configuration of an adapter can be seen in FIG. 2. There, the same designations indicate the same or corresponding parts. In the case of this configuration, the adapter 22 has a greater diameter and is intended for a different work holding fixture, in the case of which a specially shaped undercut 38 is provided instead of the notch 34. On the other hand, the receptacle 24 is shaped in the same way as in the case of the embodiment according to FIG. 1 of the adapter, and the holder 16 corresponds to the holder represented in FIG. 1. The holder 16, in particular its shank 20, has a bore or an internal thread for the fixing in the adapter 22, which in particular matches a through-bore in the adapter.

In the exemplary implement represented, a somewhat wider blank 10 is provided, which accordingly rests with a greater width on the end face 14 of the holder 16. Although the flange 18 is laterally supported, in the case of this embodiment of the adapter 22 the supporting flange 26 is not formed in the manner of a collar, but is formed directly by the side walls 36 of the adapter 22.

FIG. 3 shows the holder 16 duly clamped by claws 40 of an automatic adhesive dispenser 42. A portion of soft glue or adhesive 44 is applied on surface 14 of holder 16. A blank 12 is received in a blank supply 46 which is shown generally in FIG. 3. A supply of several blanks 12 may be used, of which each blank is intended to be attached to a holder 16.

By moving the blank 12 towards the surface 14, the adhesive 44 is spread by pressing these parts against each other. Thus, the adhesive force fixing the blank 12 on holder 16 is increased. As it is know in the art, the hardening of the adhesive 44 may be supported by heat if desired.

FIG. 4 shows a cross-section along A-A in FIG. 1. The stub of holder 16 has a generally rectangular shape with a bevel or chamfer 50 being arranged at one end thereof. The walls 25 of adapter 22 have a corresponding shape such that the position of stub 20 in the recess 24 is unique.

It should be appreciated that blanks of various sizes can accordingly be readily attached centrally on an end face of the holder and adjusted with respect to the shank of the latter. Once the relative position of the shank, which is guided in a corresponding recess in the adapter, is known for each configuration of the adapter, and consequently the corresponding work holding fixture, the number of dimensionings required according to the invention is still practicable. If, for example, 20 different work holding fixtures are to be combined with 30 different blanks, the provision of the sum of the corresponding dimensions, that is to say 50 dimensions, is required according to the invention, while theoretically, in the case of solutions without the invention that have a corresponding number of work holding fixtures and blanks, 20×30, that is to say 600, sizes would have to be 'kept in stock, which is out of the question in practice. It is surprisingly found according to the invention that the division into a holder and an adapter reduces the organizational effort involved. The above is facilitated by providing the adapter 22 with suitable indicia, for example mechanical markings, color markings, and barcodes. In addition this can also be facilitated by providing the blank 12, the holder 16, and/or the adapter 22 with a sensor, chip and/or transmitter by means of which the respective relevant type of blank, holder and/or adapter can be signaled.

Figure 5:
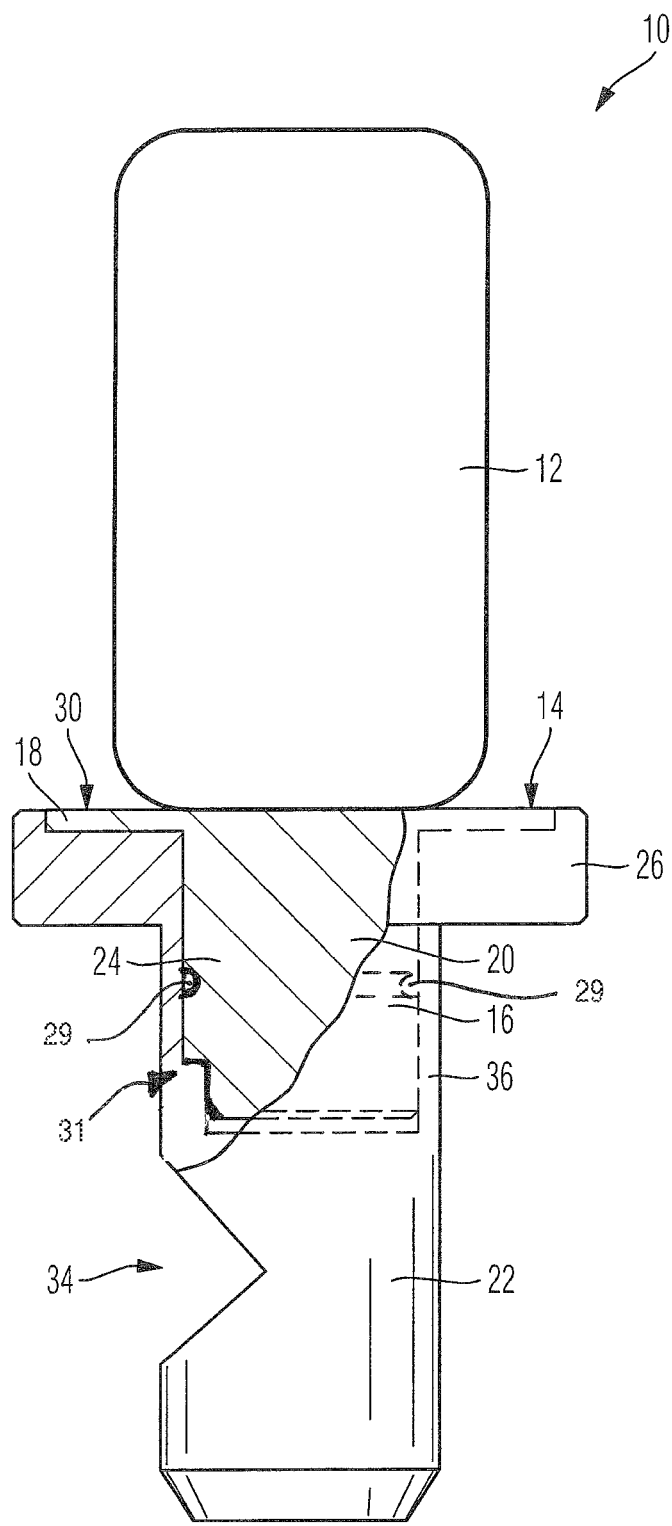
FIG. 5 shows a schematic side view of a further embodiment of a blank arrangement according to the invention.

FIG. 5 shows an alternate embodiment of the blank arrangement wherein the shank (20) of the holder (16) includes an undercut (29) which runs at least partially around shank (20). A depression (32) is shown on shank (24), which allows a form fit of the receptacle (24) with adapter (26). Alternately, the shank (24) may include a projection instead of a depression to allow a form fit of the receptacle (24) with adapter (26).

Figure 6:
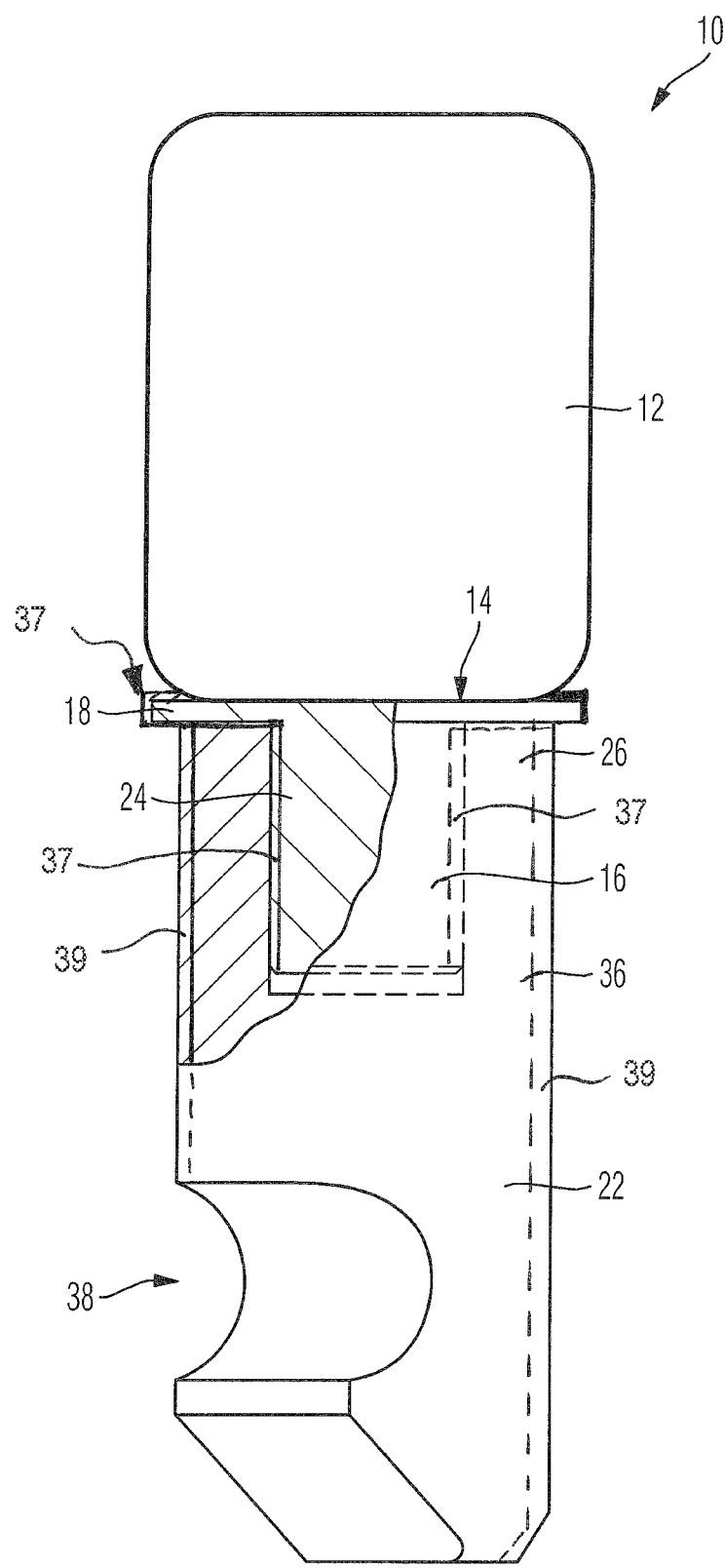
FIG. 6 shows a schematic side view of a further embodiment of a blank arrangement according to the invention.

FIG. 6 shows an alternate embodiment of the blank arrangement wherein the holder (16) is at least partially enclosed in plastic (37) and the adapter (22) is at least partially enclosed by plastic (39).

For both FIGS. 5 and 6, the same designations indicate the same or corresponding parts as in FIGS. 1 and 2.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A blank arrangement, with a blank (12) that is to be machined, made of dental material and suitable for the production of dental restoration parts, with a holder (16), which is fixedly connected to the blank (12), and an adapter (22) connected to the holder (16), the adapter (22) having an effective surface, by means of which the blank unit can be releasably fastened in or on the work holding fixture of a machining device, wherein the holder (16) comprises a shank or an insert stub (20) which extends into a receptacle (24) or blind hole of the arrangement in an upper portion of the adapter (22), wherein the blank (12) is positioned flush against the holder (16), wherein the holder (16) is received in a completely recessed manner in adapter (22), and wherein an end face of said holder (16) is formed on a flange portion (18), which is integrally connected to a shank (20) of the holder (16).

2. The blank arrangement as claimed in claim 1, wherein the holder (16) has a generally T-shaped cross-section and is intended to be inserted into said adapter (22) which also has a generally T-shaped cross-section.

3. The blank arrangement as claimed in claim 1, wherein the flange portion (18) protrudes radially beyond the shank (20) interacting with the adapter (22).

4. The blank arrangement according to claim 1, characterized in that said adapter (22), comprises a supporting flange (26) which receives and supports the flange portion (18) of said holder (16).

5. The blank arrangement according to claim 1, characterized in that said holder (16) comprises a shank (20) which fills out and stabilizes an upper portion of said adapter (22), being received in said receptacle (24) of said adapter (22).

6. The blank arrangement as claimed in one claim 1, wherein the blank (12) is bonded and/or screwed and/or welded on the end face (14) of the holder (16).

7. The blank arrangement as claimed in claim 1, wherein the holder (16) and the adapter (22) are fixedly connected to each other.

8. The blank arrangement as claimed in claim 1, wherein the shank (20) of the holder (16) interacts with said receptacle (24) or blind hole of the adapter (22) and is clamped by walls of said receptacle or blind hole.

9. The blank arrangement as claimed in claim 1, wherein the shank (20) of the holder (16), and the adapter (22) are connected to each other in a rotationally locked manner.

10. The blank arrangement as claimed in claim 1, wherein the shank (20) of the holder (16), and the adapter (22) are at least partially pressed and/or braced and/or screwed and/or adhesively bonded to each other.

11. The blank arrangement as claimed in claim 1, wherein the shank of the holder (16) has at least one undercut, which runs at least partially around it.

12. The blank arrangement as claimed in claim 1, wherein at least one of the blank (12), the holder (16) and the adapter (22) have at least one of a sensor, a transmitter and a chip.

13. The blank arrangement as claimed in claim 1, wherein at least one of the holder (16) and the adapter (22) have a predetermined breaking point, which yields under loading in the machining device.

14. The blank arrangement as claimed in claim 1, wherein, at least two adapters (22) are provided and have different effective surfaces that can be inserted into the work holding fixtures of different machining devices, and wherein the at least two adapters (22) have receptacles (24) that are the same as each other for the holder (16).

15. The blank arrangement as claimed in claim 1, wherein the shank (20) and/or the receptacle (24) have an at least partially rough and/or profiled surface.

16. The blank arrangement as claimed in claim 1, wherein the shank (20) and/or the receptacle (24) have at least one projection and/or at least one depression, which allow a form fit of these parts with respect to each other.

17. The blank arrangement as claimed in claim 1, wherein the shank (20) and/or the receptacle (24) are essentially cylindrically or conically formed and have a non-rotatable form.

18. The blank arrangement as claimed in claim 1, wherein the cross section of the shank (20) and/or the cross section of the receptacle (24) are formed such that they are round.

19. The blank arrangement as claimed in claim 1, wherein the holder (16) comprises at least partially of one of steel, plastic, aluminum, wood and glass.

20. The blank arrangement as claimed in claim 1, wherein the adapter (22) comprises at least one of steel, aluminum, and plastic.

21. The blank arrangement as claimed in claim 1, wherein the holder (16) and/or the adapter (22) are at least partially enclosed in plastic.

22. The blank arrangement as claimed in claim 1, wherein the flange portion (18) of the holder (16) is supported on the end face of the adapter (22).

23. The blank arrangement as claimed in claim 1, wherein the cross section of the shank (20) and/or the cross section of the receptacle (24) are formed such that they deviate from a circular shape.

* * * * *